United States Patent [19]
Yokoyama et al.

[11] Patent Number: 6,010,806
[45] Date of Patent: Jan. 4, 2000

[54] FLUORINE-SUBSTITUTED CYCLIC CARBONATE ELECTROLYTIC SOLUTION AND BATTERY CONTAINING THE SAME

[75] Inventors: Keiichi Yokoyama; Takako Sasano; Akio Hiwara, all of Sodegaura, Japan

[73] Assignee: Mitsui Chemicals, Inc., Tokyo, Japan

[21] Appl. No.: 08/776,755

[22] PCT Filed: Jun. 5, 1996

[86] PCT No.: PCT/JP96/01515

§ 371 Date: Feb. 6, 1997

§ 102(e) Date: Feb. 6, 1997

[87] PCT Pub. No.: WO96/41801

PCT Pub. Date: Dec. 27, 1996

[30] Foreign Application Priority Data

Jun. 13, 1995 [JP] Japan .................................. 7-146601
Sep. 6, 1995 [JP] Japan .................................. 7-143706

[51] Int. Cl.[7] ........................................... H01M 6/16
[52] U.S. Cl. ..................... 429/330; 332/326; 332/218.1; 332/231.95
[58] Field of Search ................... 429/194, 197, 429/218, 330, 231.95, 326, 218.1

[56] References Cited

U.S. PATENT DOCUMENTS 5,256,504  10/1993  Okuno et al. ........................... 429/197
5,714,280   2/1998  Nakano et al. .......................... 429/197

FOREIGN PATENT DOCUMENTS

714148A1   5/1996   European Pat. Off. .
5-74487    3/1993   Japan .
7-165750   6/1995   Japan .
7-291959  11/1995   Japan .
8-37025    2/1996   Japan .

OTHER PUBLICATIONS

Jehoshua Katzhendler et al., J. Chem. Soc. Perkin Trans II, Conformational Studies of . . . Substituted Five–Membered Cyclic Carbonates and Related Compounds by MNDO, and the X–Ray Crystal Structure of 4–Chloro–Phenyloxymethyl–1,3–dioxolan–2–one, pp. 1729–1739, 1989.

Patent Abstracts of Japan, vol. 012, No. 187 (E–615), May 31, 1988 and JP 62 290071 A (Matsushita Electric Ind Co. Ltd), Dec. 16, 1987.

Patent Abstracts of Japan, vol. 012, No. 187 (E–615), May 31, 1988 and JP 62 290072 A (Matsushita Electric Ind Co. Ltd), Dec. 16, 1987.

*Primary Examiner*—Maria Nuzzolillo
*Assistant Examiner*—Laura Weiner
*Attorney, Agent, or Firm*—Birch, Stewart, Kolasch & Birch, LLP

[57] ABSTRACT

Monofluoromethyl ethylene carbonate, difluoromethyl ethylene carbonate and trifluoromethyl ethylene carbonate are provided as novel compounds. These compounds are very useful as solvents because they are chemically and physically stable, have a high dielectric constant, can dissolve well organic substances and have a wide application temperature range. These compounds are excellent in charge and discharge cycle characteristics, have a high flash point, and are safe as non-aqueous elecytrolytes and hence, batteries using these compounds are excellent in withstand voltage and charge and discharge cycle characteristics.

11 Claims, 5 Drawing Sheets

FLUORINE-SUBSTITUTED CYCLIC CARBONATE ELECTROLYTIC SOLUTION AND BATTERY CONTAINING THE SAME

TECHNICAL FIELD

This invention relates to a fluorine-substituted cyclic carbonate and to an electrolytic solution and a battery containing the same.

BACKGROUND ART

A carbonate is a diester of carbonic acid, represented by R—O—CO—O—R' (wherein R and R' are each an alkyl group), and there are generally known chain carbonate compounds such as dimethyl carbonate, diethyl carbonate or the like and cyclic carbonate compounds such as ethylene carbonate, propylene carbonate or the like. These carbonate compounds are used as a special solvent in the fields of medicinal chemistry, agricultural chemistry, etc.; starting or intermediate material for dyes, plant protective agents, synthetic resins, etc.; agricultural chemical or drag (see Japanese Laid-open Patent Application Nos. Sho 54-125617 and Sho 54-63023).

Of these, cyclic carbonate compounds such as ethylene carbonate and propylene carbonate have excellent characteristics as a solvent in that they dissolve well various organic and inorganic substances, are chemically and physically stable and have a high dielectric constant. Therefore, they are of industrially high utility value, and it is known that they are used in not only organic solvents but also pharmaceuticals, acrylic fiber processing agents, polymer compound solvents, organic intermediate materials, electrolyte solutions for non-aqueous batteries, electrolyte solutions for capacitors and solvents for an electrochemical reaction (see Japanese Laid-open Patent Application Nos. Sho 61-64082 and Hei 1-292753).

Some halogen-substituted cyclic carbonate compounds are known as cyclic carbonate derivatives. As chlorine-substituted cyclic carbonates, there are known, for example, chloroethylene carbonate (see J. Org. Chem., 39, 38 (1974) and the specification of U.S. Pat. No. 367795), 2,3-dichlorobutylene carbonate (see Chem. Pharm. Bull., 36, 394 (1988) and Japanese Laid-open Patent Application No. Hei 2-111767), chloromethyl ethylene carbonate (see the specification of U.S. Pat. No. 4,332,729) and trichloromethyl ethylene carbonate (see Chem. Pharm. Bull., 23, 3017 (1975)). The properties as a solvent of these chlorine atom-substituted cyclic carbonates are not known.

Meanwhile, fluorine-containing carbonate compounds are not so common and such compounds as difluoroethyl carbonate as a starting material for synthetic resins (see the specification of U.S. Pat. No. 969,683); dihexafluoropropyl carbonate and ethylhexafluoropropyl carbonate as agricultural chemicals (see the specification of U.S. Pat. No. 3,359,296); and diperfluorophenyl carbonate (see the specification of U.S. Pat. No. 768,179) and methyl-2,2,2-trifluoroethyl carbonate (see Japanese Laid-open Patent Application No. Hei 6-219992) as flame retardants have been reported as chain carbonates containing fluorine.

Known examples of fluorine atom-substituted cyclic carbonates are few and in particular, a compound obtained by introducing a fluorine atom into the methyl group of methyl ethylene carbonate is totally unknown.

As described above, although known cyclic carbonates have such excellent features as solvents that they dissolve well organic and inorganic substances, are chemically and physically stable and have a high dielectric constant, they have the following problems with properties as a solvent. For instance, though ethylene carbonate has a low molecular weight, it has a freezing temperature as high as 38° C. and is solid at room temperatures. When it is used as a solvent, therefore, it must be liquefied by warming, and further, the temperature range at which it can be used as a solvent is narrow. Propylene carbonate is widely used as a non-aqueous electrolyte solvent for batteries. However, when it is used as a solvent for a lithium ion battery which uses graphite as a negative electrode material or as a solvent for a battery which uses lithium or a lithium-containing alloy as a negative electrode material, such problem is pointed out that propylene carbonate reacts with the negative electrode material to shorten the life of the battery.

Heretofore, nickel-cadmium batteries, lead batteries and the like which use an aqueous electrolytic solution have been widely used as general secondary batteries. However, new-type portable electronics such as camcorders, portable telephones, lap-top computers, etc. have been making their appearance one after another in recent years, and in this connection, a further increase in energy density is required for secondary batteries as portable power sources in order to reduce the size and weight of these electronics. Therefore, the aforesaid nickel-cadmium batteries and lead batteries are becoming unsatisfactory. Furthermore, cadmium and lead are not preferred from a viewpoint of the protection of global environment and their use has begun to be legally restricted in some countries. Under the circumstances, the development of a secondary battery which use a substitute for these materials has been desired. Attention is now paid to a non-aqueous electrolyte battery which uses a non-aqueous electrolytic solution obtained by dissolving an electrolyte in a non-aqueous solvent, as a substituent for the above nickel-cadmium batteries and lead batteries.

Since the battery in which a non-aqueous electrolytic solution is used has higher voltage and higher energy density than a battery using an aqueous electrolytic solution, it has begun to be used as a power source for electronics in civilian demands. As the non-aqueous electrolytic solution is used a mixture of a solvent having a high dielectric constant, such as propylene carbonate, γ-butyrolactone or sulfolane and an electrolyte such as lithium hexafluorophosphate.

However, an electrolytic solution for these non-aqueous solution-based batteries has electric conductivity of one to two digit lower value than that of an electrolytic solution for aqueous solution-based batteries, and this is one of factors of increase in the internal resistance of a battery. Further, a non-aqueous electrolytic solution containing a non-aqueous solvent of low withstand voltage has such a defect that the charge and discharge efficiency of a battery using such solution becomes low and its service life becomes short.

To improve the electric conductivity of a non-aqueous electrolytic solution, attempts have been made to add a cyclic ether such as 1,3-dioxolanes or tetrahydrofurans or a chain ether such as 1,2-dimethoxy ethane (DME) or diethyl ether to a cyclic carbonate such as propylene carbonate (see "Denkikagaku (Electro-chemistry)", 53, No.3, 173 (1985)).

It has been reported that a carbonate having high withstand voltage, such as diethyl carbonate, is used in place of a solvent having low withstand voltage, such as dimethoxy ethane, to increase the charge and discharge efficiency of a battery as an attempt to improve the durability of an electrolytic solution (see Japanese Laid-open Patent Application No. Hei 2-10666).

It is therefore an object of the present invention to provide a novel fluorine-substituted cyclic carbonate.

It is another object of the present invention to provide a fluorine-substituted cyclic carbonate compound useful as a solvent having such excellent properties that it is chemically and physically stable, has a high dielectric constant, is capable of dissolving well organic substances and has a wide application temperature range.

It is still another object of the present invention to provide a fluorine-substituted cyclic carbonate which gives a non-aqueous electrolytic solution having excellent withstand voltage and charge and discharge cycle characteristics, a high flash point and excellent safety.

It is a further object of the present invention to provide a non-aqueous electrolytic solution containing the fluorine-substituted cyclic carbonate of the present invention and having properties as described above.

It is a still further object of the present invention to provide a non-aqueous electrolyte battery employing the non-aqueous electrolytic solution of the present invention, which is safe, can generate high voltage, and has excellent battery performance.

The above and other objects and advantages of the present invention will become apparent from the following description.

DISCLOSURE OF THE INVENTION

According to the present invention, the above objects and advantages of the present invention can be attained firstly by a fluorine-substituted cyclic carbonate represented by the following formula (1):

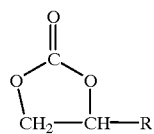

(1)

wherein R is —CFH$_2$, —CF$_2$H or —CF$_3$.

According to the present invention, the above objects and advantages can be attained secondly by a non-aqueous electrolytic solution containing a fluorine-substituted cyclic carbonate represented by the above formula (1) as an electrolyte solvent, and thirdly by a non-aqueous electrolyte battery employing this non-aqueous electrolytic solution as an electrolytic solution.

BEST MODE FOR PERFORMING THE INVENTION

Figure 1:
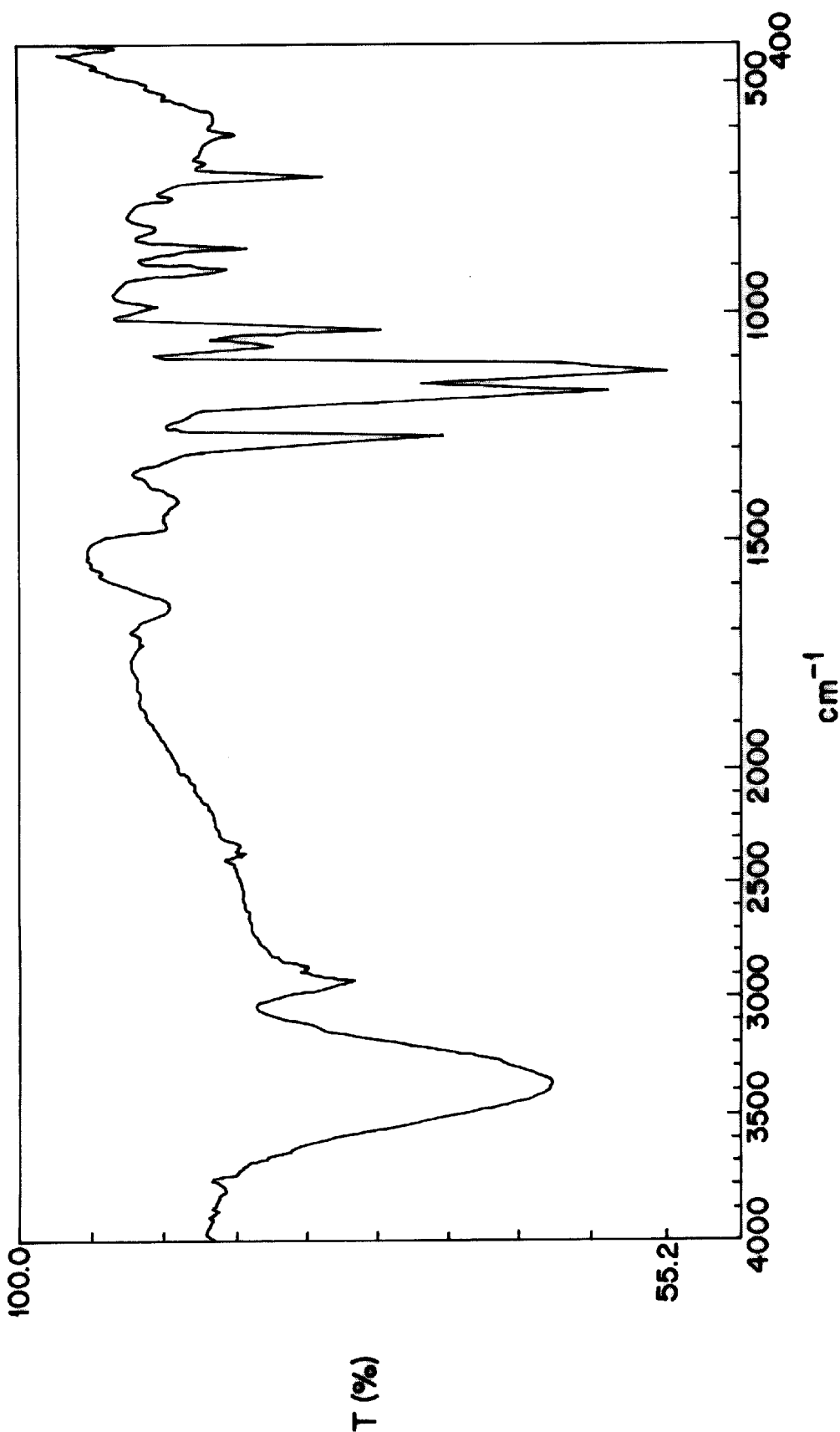
FIG. 1 is an IR absorption spectrum diagram of 3,3,3-trifluoro-1,2-propylene glycol.

Illustrative examples of the compound represented by the above formula (1) include monofluoromethyl ethylene carbonate, difluoromethyl ethylene carbonate and trifluoromethyl ethylene carbonate, which have a fluorine-containing methyl group as a substituent of a cyclic carbonate.

The compound represented by the above formula (1) can be produced by subjecting a chain carbonate such as dimethyl carbonate or diethyl carbonate and a compound obtained by substituting the hydrogen atom of the methyl group of 1,2-propylene glycol with a fluorine atom to an ester exchange reaction in the presence of a basic catalyst. Preferred examples of the basic catalyst include alkaline bases such as sodium carbonate, potassium carbonate, sodium hydroxide, sodium methoxide or the like. The fluorine atom-substituted 1,2-propylene glycol can be produced by subjecting corresponding fluorine atom-substituted propylene oxide to hydration reaction in the presence of a basic catalyst.

For instance, the production of fluoromethyl ethylene carbonate proceeds according to the following reaction scheme.

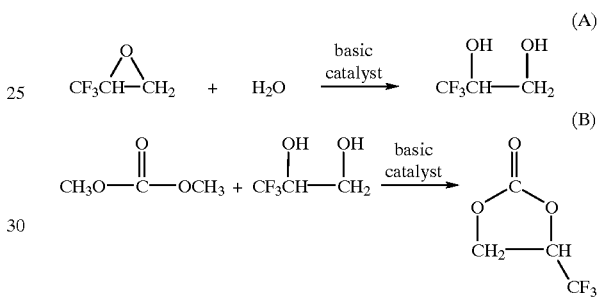

That is, as shown in the reaction formula (A), a hydration reaction of trifluoropropylene oxide is carried out in the presence of a basic catalyst such as an aqueous solution of sodium bicarbonate to produce 3,3,3-trifluoro-1,2-propylene glycol as an intermediate and then, as shown in the reaction formula (B), an ester exchange reaction of this intermediate and dimethyl carbonate is carried out to produce fluoromethyl ethylene carbonate.

The fluorine-substituted cyclic carbonate of the present invention is excellent in acid resistance, is not oxidized even when it is exposed to the air, is chemically stable and does not react with water or a highly reactive substance such as metal lithium in an ordinary storage state. It is soluble in such a solvent as ethanol, ether, acetone, ethyl acetate, dimethyl formamide, dimethyl sulfoxide, acetonitrile or the like, and can be used as a reaction solvent or cleaning solvent. Further, the fluorine-substituted cyclic carbonate of the present invention has a high dielectric constant and has the property of dissolving well not only organic substances such as ester compounds and carboxylic acids but also metal salts such as lithium hexafluorophosphate (LiPF$_6$), lithium hexafluoroarsinate (LiAsF$_6$), lithium tetrafluoroborate (LiBF$_4$), lithium trifluoromethanesulfonate (LiOSO$_2$CF$_3$), lithium perchlorate (LiClO$_4$) and lithium bistrifluoromethane sulfonylimide (LiN(SO$_2$CF$_3$)$_2$); ammonium salts such as tetraethyl ammonium tetrafluoroborate and tetraethyl ammonium hexafluorophosphate; and phosphonium salts such as tetraethyl phosphonium tetrafluoroborate. Furthermore, the fluorine-substituted cyclic carbonate of the present invention is physically safe, is hardly thermally decomposed, is flame retardant, and is hardly oxidized or reduced electrochemically. In addition, it is further useful as a solvent since it is highly stable chemically and physically, has a high dielectric constant and a low melting point, and can dissolve well organic substances.

Accordingly, the fluorine-substituted cyclic carbonate of the present invention is useful as a solvent for use in an electrolytic solution for batteries, capacitors and an electrochemical reaction. Also, it is expected to be used as an agricultural chemical, pharmaceutical, acrylic fiber processing agent, solvent for polymer compound, and organic intermediate material.

Therefore, according to the present invention, there are provided a non-aqueous electrolytic solution containing the fluorine-substituted cyclic carbonate of the present invention as an electrolyte solvent and a non-aqueous electrolyte battery comprising this non-aqueous electrolytic solution as an electrolytic solution.

Specific examples of the fluorine-substituted cyclic carbonate represented by the above formula (1) include monofluoromethyl ethylene carbonate, difluoromethyl ethylene carbonate and trifluoromethyl ethylene carbonate as described above, and trifluoromethyl ethylene carbonate is the most preferred of these compounds. The compounds may be used alone or in combination of two or more.

As the electrolyte solvent in the present invention may be used a fluorine-substituted cyclic carbonate represented by the above formula (1) or a mixture thereof with another solvent. Illustrative examples of the solvent to be mixed include other cyclic carbonates such as ethylene carbonate, propylene carbonate, butylene carbonate and vinylene carbonate; cyclic esters such as γ-butyrolactone; chain carbonates such as dimethyl carbonate, diethyl carbonate, methyl ethyl carbonate, methyl propyl carbonate, methyl isopropyl carbonate and ethyl butyl carbonate; chain esters such as methyl formate, ethyl formate, propyl formate, methyl butyrate, ethyl butyrate, propyl butyrate, methyl propionate, ethyl propionate and propyl propionate; ethers such as 1,3-dioxolane, tetrahydrofuran, 1,2-dimethoxy ethane and diethyl ether; and sulfur-containing compounds such as sulfolane. They may be used alone or in combination of two or more.

A mixed solvent of a fluorine-substituted cyclic carbonate and a chain carbonate is particularly preferably used in the non-aqueous electrolytic solution of the present invention. The chain carbonate used in the mixed solvent is preferably a carbonate having 3 to 6 carbon atoms, more preferably a carbonate having 3 to 4 carbon atoms. Illustrative examples of the above carbonate include dimethyl carbonate, methyl ethyl carbonate, methyl propyl carbonate and diethyl carbonate. In addition, a carbonate having a halogen atom-substituted alkyl group, as disclosed in Japanese Laid-open Patent Application No. Hei 6-219992, may also be used as the carbonate to be mixed. Illustrative examples of the carbonate include methyl 2,2,2-trifluoroethyl carbonate, methyl 2,2,3,3-tetrafluoropropyl carbonate, ethyl 2,2,2-trifluoroethyl carbonate or the like.

The mixing ratio of the cyclic carbonate represented by the above formula (1) and the other solvent in the non-aqueous electrolytic solution of the present invention is not particularly limited, while the fluorine-substituted cyclic carbonate represented by the above formula (1) is preferably contained in an amount of 10% by volume or more, more preferably 20 to 60% by volume, based on the sum of it and the other solvent.

As an electrolyte used in the non-aqueous electrolytic solution of the present invention may be used an electrolyte generally used in a non-aqueous electrolytic solution. As an electrolyte used in the electrolytic solution of a non-aqueous electrolyte battery may be used an electrolyte used in a general battery electrolytic solution, e.g., lithium salts containing a halogen atom, such as lithium hexafluorophosphate ($LiPF_6$), lithium tetrafluoroborate ($LiBF_4$), lithium perchlorate ($LiClO_4$), lithium hexafluoroarsenate ($LiAsF_6$), lithium trifluoromethane sulfonate ($LiOSO_2CF_3$), lithium bistrifluoromethane sulfonylimide ($LiN(SO_2CF_3)_2$), $LiC(SO_2CF_3)_3$, $LiAlCl_3$, $LiSiF_6$ and the like. Of these, $LiPF_6$, $LiBF_4$, $LiOSO_2CF_3$, $LiN(SO_2CF_3)_2$, $LiC(SO_2CF_3)_3$ and $LiClO_4$ are preferred. As an electrolyte used in an electrolytic solution for an electric double-layer capacitor may be used, for example, an electrolyte generally used in an electrolytic solution for an electric double-layer capacitor, e.g., an ammonium salt such as tetramethyl ammonium tetrafluoroborate ($Me_4NBF_4$), tetraethyl ammonium tetrafluoroborate ($Et_4NBF_4$), tetramethyl ammonium hexafluorophosphate ($Me_4NPF_6$), tetraethyl ammonium hexafluorophosphate ($Et_4NPF_6$); and a phosphonium salt such as tetramethyl phosphonium tetrafluoroborate ($Me_4PBF_4$), tetraethyl phosphonium tetrafluoroborate ($Et_4PBF_4$), tetramethyl phosphonium tetrafluorophosphate ($Me_4PPF_6$), tetraethyl phosphonium tetrafluorophosphate ($Et_4PPF_6$) and the like. In the above chemical formula, Me and Et stand for methyl group and ethyl group, respectively.

The concentration of the electrolyte dissolved in the solvent is generally 0.1 to 3 moles/L, preferably 0.5 to 1.5 mole/L.

By containing a fluorine-substituted cyclic carbonate represented by the above formula (1), the non-aqueous electrolytic solution of the present invention can have high withstand voltage and excellent charge and discharge cycle characteristics. The non-aqueous electrolytic solution of the invention can be used as an electrolytic solution for a non-aqueous electrolyte battery, electric double-layer capacitor or the like by suitably selecting an electrolyte.

A description is subsequently given of the battery of the present invention.

The battery of the present invention uses the above non-aqueous electrolytic and consists of at least a positive electrode, a negative electrode and a separator.

The active material for the negative electrode is preferably a metal lithium, a lithium alloy or a carbon material which can dope or undope lithium ions. A carbon material which can dope or undope lithium ions is particularly preferred. The carbon material may be either graphite or amorphous carbon, and any carbonaceous materials such as activated carbon, carbon fibers, carbon black, mesocarbon microbeads and the like can be used.

The active material used for the positive electrode is a composite oxide of lithium and a transition metal. Preferred examples of the composite oxide include $LiCoO_2$, $LiMnO_2$, $LiMn_2O_4$, $LiNiO_2$ and the like.

Other active materials which can be used in the positive electrode include transition metal oxides or sulfides such as $MoS_2$, $TiS_2$, $MnO_2$, $V_2O_5$ or the like; conductive polymers such as polyaniline, polypyrrole or the like, disulfide compounds, which are electrolytically polymerized or de-polymerized reversibly.

The shape and form of the battery of the present invention are not particularly limited. The battery of the present invention may be cylindrical, square, coin-shaped, card-shaped, large-sized or the like, from which you may select a desired one within the scope of the invention.

Since the non-aqueous electrolyte battery of the present invention contains the above non-aqueous electrolytic solution as an electrolytic solution, it can be used as a non-aqueous secondary battery which can generate high voltage and is free from deterioration in battery performance even after repetitions of charging and discharging.

It should be understood that the previously-given description of the non-aqueous electrolytic solution is applied to the non-aqueous electrolytic solution used in the battery of the present invention without any alteration.

The non-aqueous electrolytic solution of the present invention has a higher flash point than that of a conventionally-used solvent such as 1,3-dioxolane, tetrahydrofuran, 1,2-dimethoxyethane (DME) or diethyl ether and is excellent in safety; and the battery of the present invention using the non-aqueous electrolytic solution of the present invention is excellent in withstand voltage and charge and discharge cycle characteristics (that is, almost no reduction in battery performance after repetitions of charging and discharging) and has high energy density.

The following examples are given to further illustrate the present invention.

EXAMPLE 1 AND COMPARATIVE EXAMPLES 1 AND 2

Production of Trifluoromethyl Ethylene Carbonate

1) Production of 3,3,3-trifluoro-1,2-propylene glycol

Figure 2:
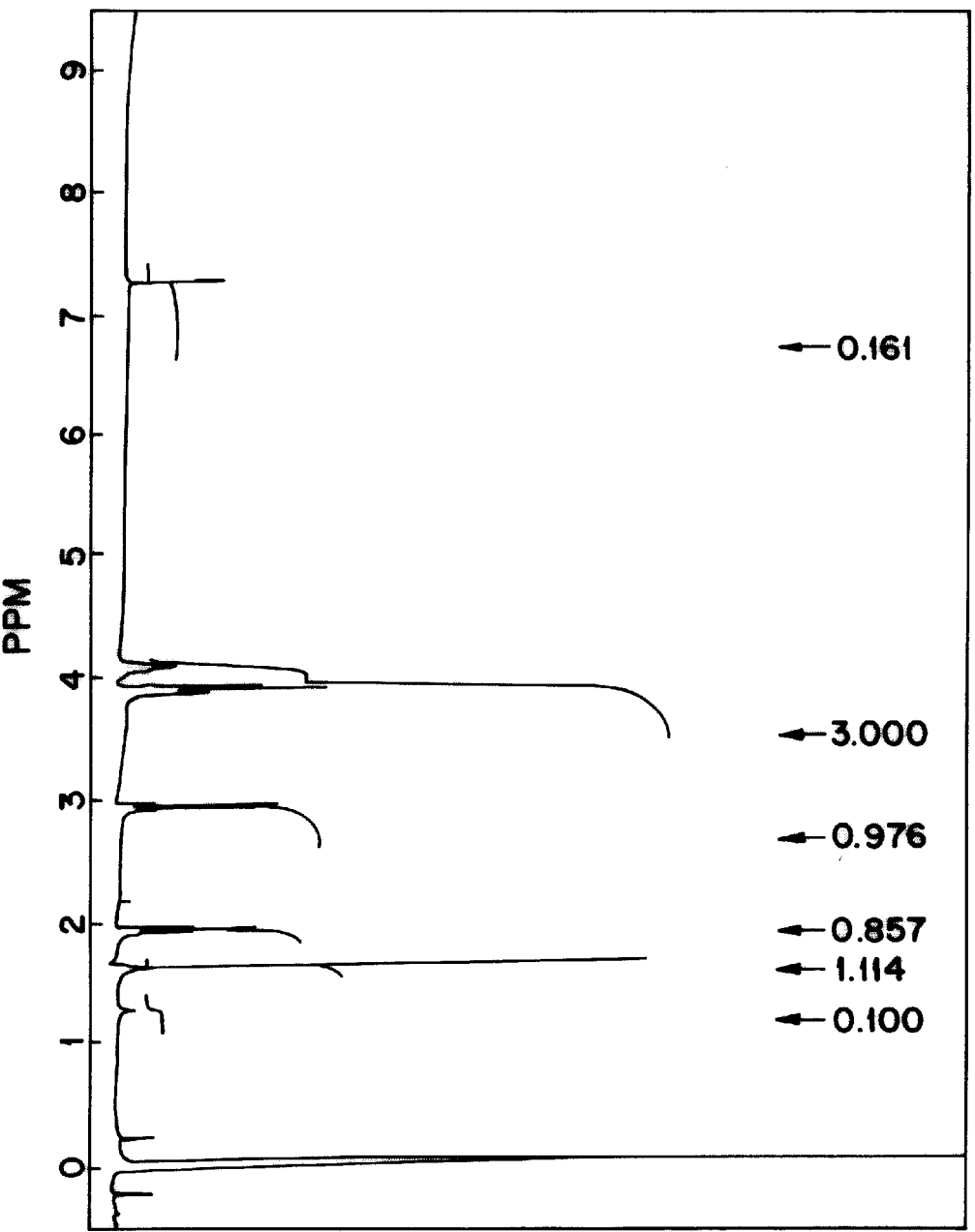
FIG. 2 is an NMR absorption spectrum diagram of 3,3,3,-trifluoro-1,2-propylene glycol.

200 Milliliters of a 3% aqueous solution of sodium hydrogencarbonate was charged into a 1-liter flask equipped with a dropping funnel and a dry ice condenser, and heated to 40° C. 100 Grams (0.90 mol) of 3,3,3-trifluoro-1,2-propylene oxide was dropped into the flask from the dropping funnel and then stirred for 48 hours to carry out a reaction. After addition of ethyl acetate, the reaction product was shaken for extraction. When the resultant organic layer was dried and the solvent was distilled off from the organic layer with a rotary evaporator, crude crystals separated out. 84 grams (yield: 71%) of crude crystals were obtained by filtering a slurry. The crude crystals were recrystallized from hexane to isolate pure 3,3,3-trifluoro-1,2-propylene glycol. The produced compound had the following IR and NMR absorption peaks which are shown in FIGS. 1 and 2.

IR (KBr tablet method, $cm^{-1}$): 3380 (O—H), 2924 (C—H), 1275, 1179, 1139, 1068, 1032, 900, 855, 710. NMR ($CDCl_3$ solution, δ ppm): 1.94 (t, 1H, J=7 Hz, COH), 2.94 (d, 1H, J=8 Hz, C($CF_3$)OH), 3.88 (t, 2H, J=7 Hz, $CH_3$), 4.09 (m, 1H, $CHCF_3$) melting point: 55.0–55.6° C.

2) Production of trifluoromethyl ethylene carbonate

Figure 3:
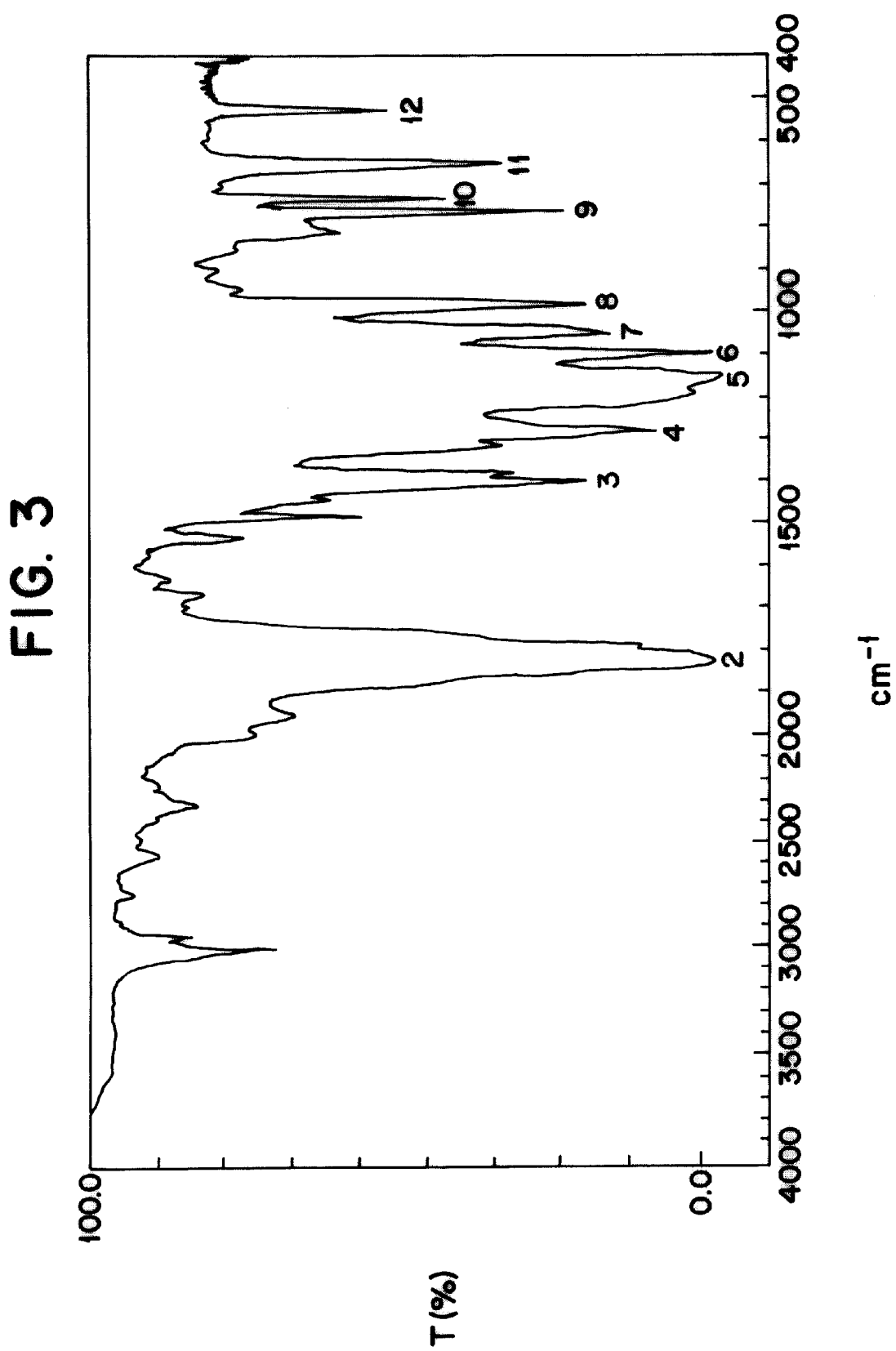
FIG. 3 is an IR absorption spectrum diagram of trifluoromethyl ethylene carbonate.
Figure 4:
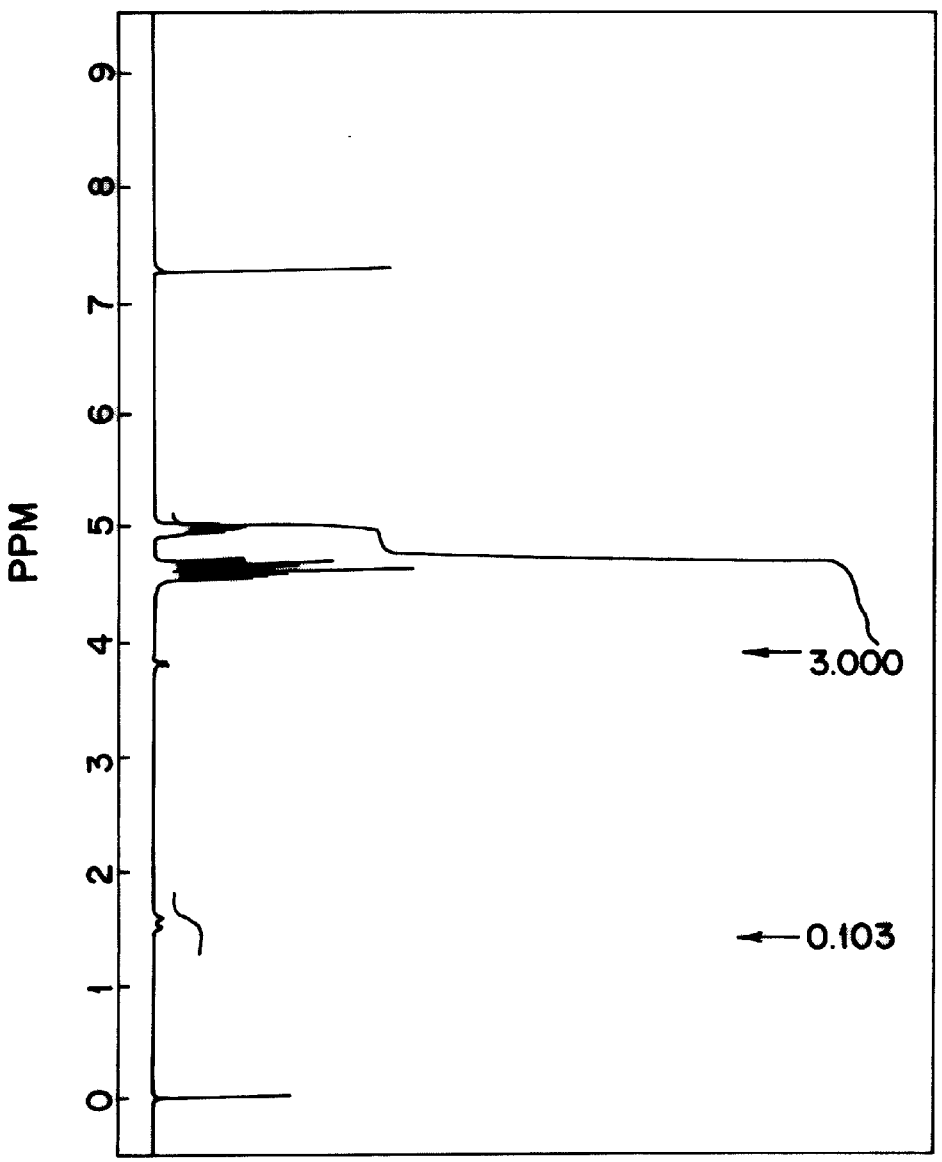
FIG. 4 is an NMR absorption spectrum diagram of trifluoromethyl ethylene carbonate.

84 Grams (0.64 mol) of 3,3,3-trifluoro-1,2-propylene glycol, 2 liters of dimethyl carbonate and 14 g (0.10 mol) of potassium carbonate were charged into a 3-liter flask equipped with a 20-stage distillation column. The flask was heated to 110° C. to carry out a reaction for 24 hours while distilling off methanol from the distillation column. The flask was cooled to room temperature, and the reaction product was caused to pass through a silica gel column to remove potassium carbonate. The organic layer was distilled to obtain 57 g (yield of 57%) of trifluoromethyl ethylene carbonate (trifluoropropylene carbonate) as an achromatic liquid. The physical properties (melting point, boiling point at 20 mmHg, dielectric constant, viscosity) of the substance are shown in Table 1. The structure of the produced compound was determined from IR and NMR absorption spectra shown in FIGS. 3 and 4. The IR and NMR absorption peaks are as follows.

IR (neat, $cm^{-1}$): 3000 (C—H), 1832 (C=O), 1405, 1283, 1156, 1099, 1050, 985, 764, 732, 651, 525. NMR ($CDCl_3$ solution, δ ppm): 4.57 (q, 1H, J=7 Hz, CH), 4.68 (t, 1H, J=8 Hz, CH), 4.97 (m, 21H, $CHCF_3$)

Table 1 shows also the physical properties of propylene carbonate and ethylene carbonate for comparison.

TABLE 1

| Example No. | Compound | Melting point (° C.) | Boiling point (° C.) | Dielectric constant | Viscosity (cP) |
|---|---|---|---|---|---|
| Ex. 1 | trifluoromethyl ethylene carbonate | −4 | 120 (50 mmHg) | 62.5 | 4.6 |
| Comp. Ex. 1 | propylene carbonate | −49 | 242 | 67 | 2.5 |
| Comp. Ex. 2 | ethylene carbonate | 38 | 248 | 95 | 1.9* |

Ex. = Example, Comp. Ex. = Comparative Example
*Viscosity was measured at 40° C.

EXAMPLE 2 AND COMPARATIVE EXAMPLE 3

3.8 Grams (25 mmols) of lithium hexafluorophosphate ($LiPF_6$) was dissolved in a mixed solvent of the compound obtained in Example 1 and propylene carbonate (volume ratio of 1:1) to prepare 25 ml of an electrolytic solution. The electric conductivity of the electrolytic solution was measured at 10 kHz using an impedance meter. Platinum was used in a working electrode and a counter electrode, and metal lithium was used in a reference electrode to measure the withstand voltage of the electrolytic solution with a potentiostat. The measurement was carried out by charging the above electrolytic solution into a 3-electrode voltage measurement cell and applying a potential of 50 mV/sec with a potentiostat. A range at which a decomposition current of 0.1 mA or more did not run was taken as a withstand voltage. The measurement results are shown in Table 2. The withstand voltage of an electrolytic solution containing only propylene carbonate as a solvent was measured likewise and the measurement result is also shown in Table 2.

TABLE 2

| | Compound | Electric conductivity (mS/cm) | Withstand voltage (V) |
|---|---|---|---|
| Example 2 | trifluoromethyl ethylene carbonate + PC | 7.6 | 6.5 |
| Comparative Example 3 | propylene carbonate (PC) | 8.2 | 6.2 |

Since the cyclic carbonate compound of the present invention has high withstand voltage as is apparent from Table 2, it can be advantageously used as an electrolyte solvent for a battery.

EXAMPLE 3 TO 5 AND COMPARATIVE EXAMPLE 4

Electric Conductivity and Withstand Voltage 3.8 Grams (25 mmols) of lithium hexafluorophosphate ($LiPF_6$) was dissolved in a mixed solvent of dimethyl carbonate (DMC) and each of three cyclic carbonate compounds shown in Table 3 (volume ratio of 1:1) to prepare 25 ml of an electrolytic solution (electrolyte concentration of 1.0 mol/L). The electric conductivity and withstand voltage of each of the thus produced electrolytic solutions were measured. The electric conductivity was measured at 10 kHz using an impedance meter. The measurement of the withstand voltage of the electrolytic solution was carried out by charging each of the above electrolytic solutions into a three-electrode withstand voltage measurement cell using glassy carbon in a working electrode, platinum in a counter electrode and metal lithium in a reference electrode, and applying a potential of 50 mV/sec with a potentiogarvanostat. A range at which an oxidation decomposition current of 0.1 mA or more did not run was taken as withstand voltage based on the potential of metal lithium. The measurement results are shown in Table 3. As is seen from the table, the compounds of Examples showed an electric conductivity of 7.6 mS/cm or more which was a practical application level.

The electric conductivity and withstand voltage of an electrolytic solution containing a mixed solvent of propylene carbonate and dimethyl carbonate were measured as Comparative Example 4. The results are also shown in Table 3.

TABLE 3

|  | Cyclic carbonate compound | Electric conductivity (mS/cm) | Withstand voltage (V) |
| --- | --- | --- | --- |
| Example 3 | trifluoromethyl ethylene carbonate | 7.6 | 6.5 |
| Example 4 | difluoromethyl ethylene carbonate | 7.8 | 6.4 |
| Example 5 | monofluoromethyl ethylene carbonate | 8.0 | 6.3 |
| Comparative Example 4 | propylene carbonate | 10.7 | 6.2 |

EXAMPLES 6 TO 8 AND COMPARATIVE EXAMPLE 5

Reactivity with Positive Electrode

As a positive electrode a mixture consisting of 85 parts by weight of $LiCoO_2$, 12 parts by weight of graphite and 3 parts by weight of a fluororesin was press-molded, and was charged to 4.5 V using Li as a counter electrode. This positive electrode was cleaned with a carbonate-based solvent, dried, pulverized and mixed with an electrolytic solution to prepare a sample. The positive electrode material/electrolytic solution mixture was put in a stainless steel container which was then sealed, and DSC measurement was carried out by elevating the temperature inside the container from 0 to 400° C. at a rate of 10° C./min. The exothermic reaction starting temperature was set at a peak rising temperature. The results are shown in Table 4.

TABLE 4

|  | Electrolyte solvent composition (Electrolyte:$LiPF_6$ (1M)) | Exothermic reaction starting temperature (° C.) |
| --- | --- | --- |
| Example 6 | trifluoromethyl ethylene carbonate | 290 |
| Example 7 | difluoromethyl ethylene carbonate | 280 |
| Example 8 | monofluoromethyl ethylene carbonate | 260 |
| Comparative Example 5 | propylene carbonate | 250 |

EXAMPLE 9

Life of Battery Cycle

Figure 6:
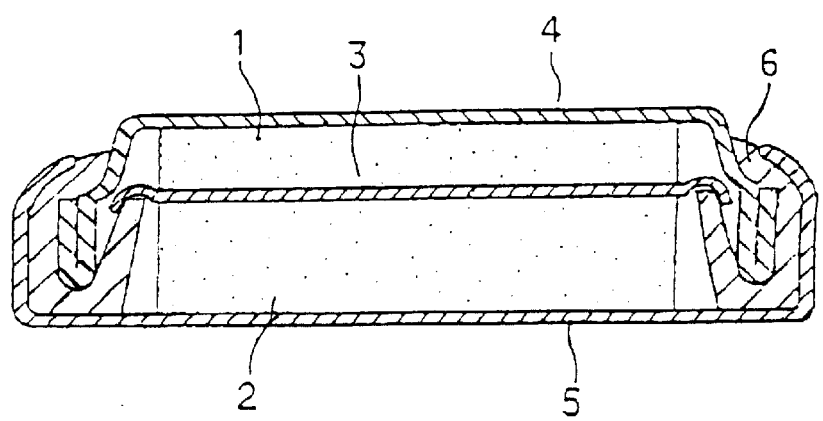
FIG. 6 is a schematic sectional view of a non-aqueous electrolyte battery according to an embodiment of the present invention.

A coin-shaped non-aqueous electrolyte battery having an outer diameter of 20 mm and a height of 2.5 mm as shown in FIG. 6 was made. Lithium metal was used as a negative electrode 1 and a press molding of a mixture consisting of 85 parts by weight of $LiCoO_2$, 12 parts by weight of graphite as a conducting agent and 3 parts by weight of a fluororesin as a binder was used as a positive electrode 2. These materials constituting the negative electrode 1 and positive electrode 2 were press contacted to a negative electrode can 4 and a positive electrode can 5 through a porous separator made from polypropylene. As an electrolytic solution for this battery, a solution of 1.0 mol/L $LiPF_6$ dissolved in a mixed solvent of trifluoromethyl ethylene carbonate (TFMEC) and dimethyl carbonate (DMC) (volume ratio of 1:1) was used and injected from a sealing gasket 6.

The charge and discharge efficiency of the thus produced battery was measured when it was charged with a current of 1.0 mA as the upper limit voltage of 4.1 V for 10 hours and subsequently discharged until the voltage became to 3.0 V with a current of 1.0 mA. The cycle of charging and discharging as described above was repeated a predetermined number of times to observe changes in charge and discharge efficiency. The results are shown in FIG. 5 in which charge and discharge efficiency is plotted with respect to the number of the cycles.

A coin-shaped battery as comparative example was manufactured in the same manner as in the case of use of trifluoromethyl ethylene carbonate except that a mixed solvent (volume ratio of 1:1) of propylene carbonate (PC) and dimethyl carbonate (DMC) was used as an electrolyte solvent and was measured for its charge and discharge efficiency. The results are shown in FIG. 5.

Figure 5:
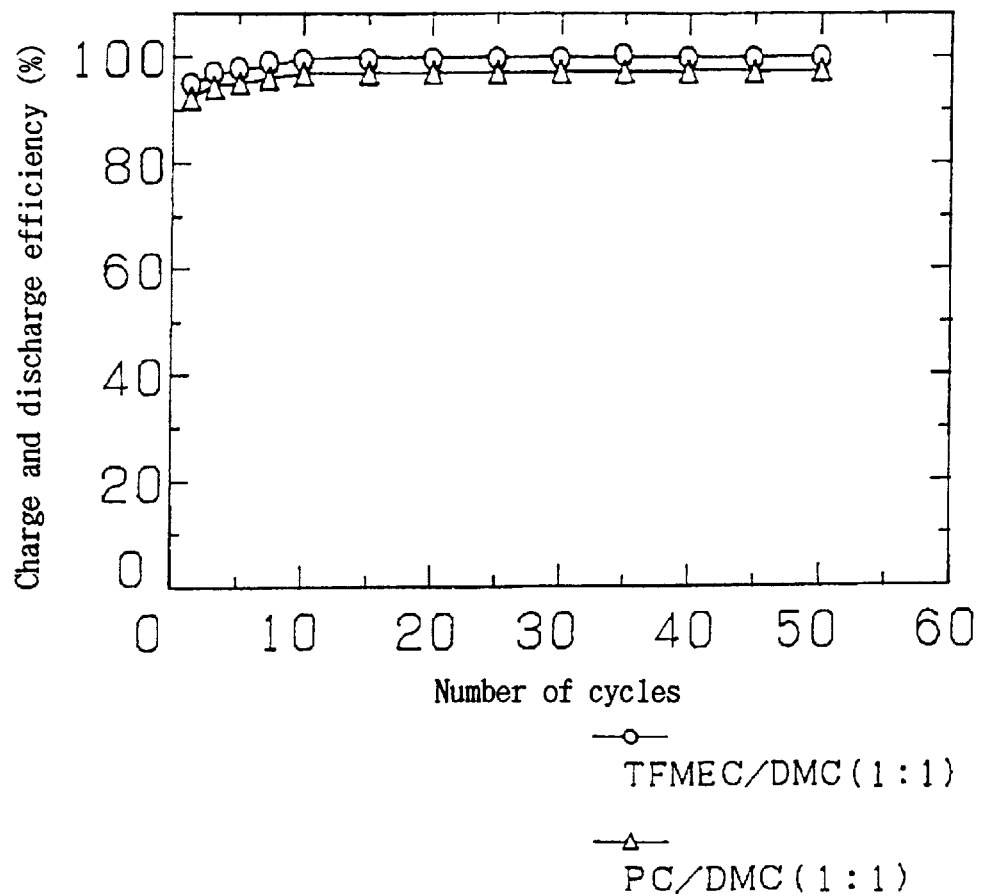
FIG. 5 is a diagram showing charge and discharge cycle characteristics of a battery using the non-aqueous electrolytic solution of the present invention.

As is evident from FIG. 5, the battery which used the electrolytic solutions of the present Example retained a high energy density even when it was charged to a high voltage of 4 V or more, and showed excellent cycle characteristics.

We claim:

1. A non-aqueous electrolytic solution containing as an electrolyte solvent a fluorine-substituted cyclic carbonate represented by the following formula (1):

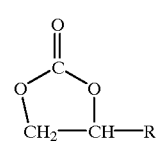

(1)

wherein R is $—CFH_2$, $—CF_2H$ or $—CF_3$.

2. A non-aqueous electrolytic solution according to claim 1, wherein the fluorine-substituted cyclic carbonate is trifluoromethyl ethylene carbonate which is a compound of the above formula (1) in which R is $CF_3$.

3. A non-aqueous electrolytic solution according to claim 1 which contains a combination of a chain carbonate and a fluorine-substituted cyclic carbonate represented by the above formula (1) as an electrolyte solvent.

4. A non-aqueous electrolytic solution according to claim 3, wherein the electrolyte solvent contains at least 10% by volume of the fluorine-substituted cyclic carbonate based on the total of the fluorine-substituted cyclic carbonate and the chain carbonate.

5. A non-aqueous electrolytic solution according to claim 1 which contains $LiPF_6$ as an electrolyte.

6. A non-aqueous electrolyte battery which uses a non-aqueous electrolytic solution containing, as an electrolyte solvent, a fluorine-substituted cyclic carbonate represented by the following formula (1):

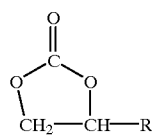

(1)

wherein R is —CFH$_2$, —CF$_2$H or —CF$_3$.

7. A non-aqueous electrolyte battery according to claim 6, wherein the fluorine-substituted cyclic carbonate is trifluoromethyl ethylene carbonate which is a compound of the above formula (1) in which R is CF$_3$.

8. A non-aqueous electrolyte battery according to claim 6 which contains a combination of a chain carbonate and a fluorine-substituted cyclic carbonate represented by the above formula (1) as an electrolyte solvent.

9. A non-aqueous electrolyte battery according to claim 6 which contains at least 10% by volume of the fluorine-substituted cyclic carbonate based on the total of the fluorine-substituted cyclic carbonate and the chain carbonate.

10. A non-aqueous electrolyte battery according to claim 6 which contains LiPF$_6$ as an electrolyte.

11. A non-aqueous electrolyte battery according to claim 6 which has a negative electrode containing a negative electrode active material selected from the group consisting of metal lithium, lithium alloys and carbon materials capable of doping or undoping lithium ions and a positive electrode containing a positive electrode active material of a composite oxide comprising lithium and a transition metal.

* * * * *

UNITED STATES PATENT AND TRADEMARK OFFICE
CERTIFICATE OF CORRECTION

PATENT NO. : 6,010,806
DATED : January 4, 2000
INVENTOR(S) : Yokoyama et al.

It is certified that error appears in the above-identified patent and that said Letters Patent is hereby corrected as shown below:

ON THE TITLE PAGE

In category "[30] Foreign Application Priority Data", please change the information for the second priority application as follows:

"Sep. 6, 1995 [JP] Japan .................... 7-143706"

to

-- June 9, 1995 [JP] Japan ....................7-143706 --.

Signed and Sealed this

Eighth Day of May, 2001

*Attest:*

NICHOLAS P. GODICI

*Attesting Officer*    *Acting Director of the United States Patent and Trademark Office*